(12) United States Patent
Bendall et al.

(10) Patent No.: US 8,976,363 B2
(45) Date of Patent: *Mar. 10, 2015

(54) SYSTEM ASPECTS FOR A PROBE SYSTEM THAT UTILIZES STRUCTURED-LIGHT

(75) Inventors: Clark Alexander Bendall, Syracuse, NY (US); Kevin George Harding, Niskayuna, NY (US); Thomas Karpen, Skaneateles, NY (US); Guiju Song, Shanghai (CN); Li Tao, ShangHai (CN)

(73) Assignee: General Electric Company, Schenectady, NY (US)

( * ) Notice: Subject to any disclaimer, the term of this patent is extended or adjusted under 35 U.S.C. 154(b) by 540 days.

This patent is subject to a terminal disclaimer.

(21) Appl. No.: 13/334,239

(22) Filed: Dec. 22, 2011

(65) Prior Publication Data

US 2012/0188560 A1    Jul. 26, 2012

Related U.S. Application Data

(63) Continuation of application No. 12/249,513, filed on Oct. 10, 2008, now Pat. No. 8,107,083.

(51) Int. Cl.
*G01B 9/02*       (2006.01)
*G01B 11/25*     (2006.01)
(Continued)

(52) U.S. Cl.
CPC .............. *G01B 11/25* (2013.01); *G01N 21/954* (2013.01); *G06T 7/0057* (2013.01); *G01N 2021/9544* (2013.01)
USPC ........................................................ 356/457

(58) Field of Classification Search
CPC .............................. G01B 11/25; G01B 11/254
USPC ............. 356/457, 458, 2, 605, 489, 496, 511, 356/512, 618
See application file for complete search history.

(56) References Cited

U.S. PATENT DOCUMENTS

| 5,135,308 A | 8/1992 | Kuchel |
| 5,434,669 A | 7/1995 | Tabata et al. |

(Continued)

FOREIGN PATENT DOCUMENTS

| CN | 101726263 A | 6/2010 |
| EP | 2272417 A1 | 1/2011 |

OTHER PUBLICATIONS

Search Report and Written Opinion from EP Application No. 12166473.4 dated Jul. 27, 2012.

(Continued)

*Primary Examiner* — Hwa Lee
(74) *Attorney, Agent, or Firm* — GE Global Patent Operation; Mark A. Conklin

(57) ABSTRACT

A probe system includes an imager and an inspection light source. The probe system is configured to operate in an inspection mode and a measurement mode. During inspection mode, the inspection light source is enabled. During measurement mode, the inspection light source is disabled, and a structured-light pattern is projected. The probe system is further configured to capture at least one measurement mode image. In the at least one measurement mode image, the structured-light pattern is projected onto an object. The probe system is configured to utilize pixel values from the at least one measurement mode image to determine at least one geometric dimension of the object. A probe system configured to detect relative movement between a probe and the object between captures of two or more of a plurality of images is also provided.

38 Claims, 6 Drawing Sheets

(51) Int. Cl.
    *G01N 21/954* (2006.01)
    *G06T 7/00* (2006.01)

(56) References Cited

U.S. PATENT DOCUMENTS 5,847,832 A     12/1998   Liskow et al.
8,107,083 B2 *   1/2012   Bendall et al. ................ 356/457
2006/0282009 A1   12/2006   Oberg et al.
2009/0225320 A1   9/2009   Bendall et al.
2009/0225321 A1   9/2009   Bendall et al.
2009/0225329 A1   9/2009   Bendall et al.

OTHER PUBLICATIONS

Unofficial Translation of CN Office Action for corresponding CN Application No. 200910166922.9 dated Nov. 15, 2013.

* cited by examiner

SYSTEM ASPECTS FOR A PROBE SYSTEM THAT UTILIZES STRUCTURED-LIGHT

CROSS-REFERENCE TO RELATED APPLICATIONS

This application is a Continuation of and claims priority from U.S. Ser. No. 12/249,513, now U.S. Pat. No. 8,107,083, filed Oct. 10, 2008 entitled System Aspects for a Probe System that Utilizes Structured-Light which is incorporated herein by reference.

BACKGROUND OF THE INVENTION

1. Field of the Invention

The subject matter described herein relates generally to borescopes and endoscopes, and more particularly, to a borescope/endoscope which provides 3D surface mapping and dimensional measurement.

2. Related Art

Borescopes and endoscopes are typically used for inspection inside a remote cavity. Most borescopes/endoscopes, referred to herein as a probe, employ an external light source coupled to fiber optic bundles in the probe to provide illumination of a remote object or surface at the distal end. When the object is illuminated, an internal image is formed by a lens system on an image sensor, and the image is relayed to a connected display, such as a video screen. The image sensor may be located at the proximal end of the probe, as with an optical rigid borescope or fiberscope, or at the distal end as with a video borescope or endoscope. Such systems are often used to inspect inaccessible locations for damage or wear or to verify that parts have been properly manufactured or assembled. Among other things, it is desirable to obtain dimensional measurements to verify that damage or wear does not exceed an operational limit or that a manufactured part or assembly meets its specifications. It may also be desirable to produce a 3D model or surface map for comparison to a reference, 3D viewing, reverse engineering, or detailed surface analysis.

Phase-shift technology is well suited to addressing these measurement needs, but its implementation in a borescope or endoscope presents numerous system-level challenges. It is desirable to address these challenges in a manner that yields a reliable and easy-to-use system.

BRIEF DESCRIPTION OF THE INVENTION

In accordance with an embodiment of the present invention, a probe system comprises an imager and an inspection light source. The probe system is configured to operate in an inspection mode and a measurement mode. During inspection mode, the inspection light source is enabled. During measurement mode, the inspection light source is disabled, and a structured-light pattern is projected. The probe system is further configured to capture at least one measurement mode image. In the at least one measurement mode image, the structured-light pattern is projected onto an object. The probe system is configured to utilize pixel values from the at least one measurement mode image to determine at least one geometric dimension of the object.

In another embodiment of the invention, a probe system comprises an imager, and the probe system is configured to operate in an inspection mode and a measurement mode. Diffuse illumination light is projected during inspection mode, and a structured-light pattern is projected during measurement mode. The probe system is further configured to capture at least one measurement mode image. In the at least one measurement mode image, the structured-light pattern is projected onto an object. The probe system is configured to utilize pixel values from the at least one measurement mode image to determine at least one geometric dimension of the object. The probe system is also configured to detect relative movement between a probe and the object between captures of two or more of a plurality of images.

BRIEF DESCRIPTION OF THE DRAWINGS

The following detailed description is made with reference to the accompanying drawings, in which.

DETAILED DESCRIPTION OF THE PREFERRED EMBODIMENT

Figure 1:
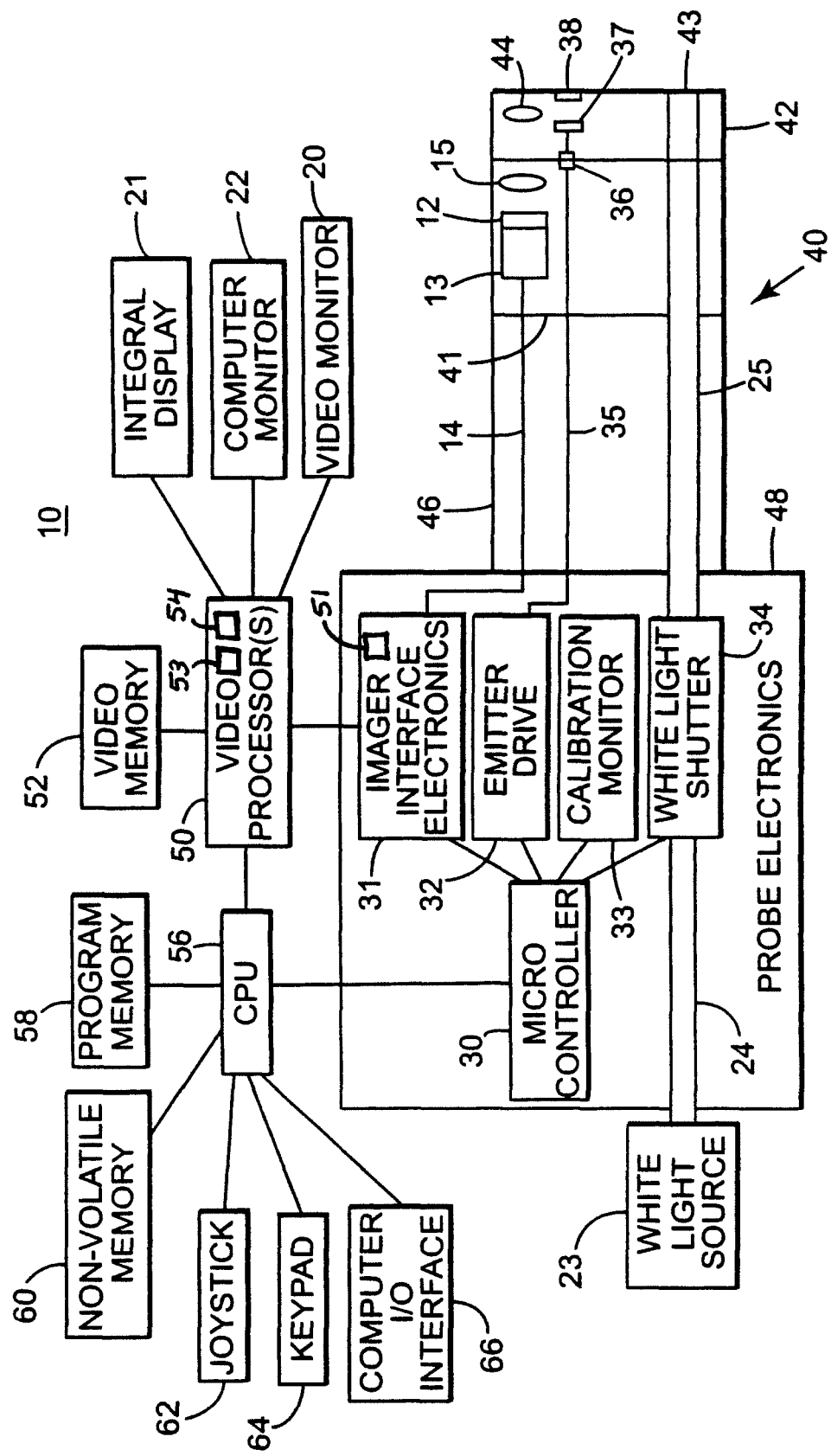
FIG. 1 is a schematic diagram of a borescope/endoscope system in accordance with an embodiment of the present invention.

Illustrated in FIG. 1, a borescope/endoscope system or probe system 10 according to an embodiment of the invention is shown. An insertion tube 40 comprises elongated portion 46 and detachable distal tip 42. Elongated portion 46 comprises a main long, flexible portion, a bending neck, and a camera head. Delineation line 41 shows where the camera head starts on elongated portion 46. The camera head of elongated portion 46 typically includes at least imager 12, electronics 13, and probe optics 15. Detachable distal tip 42 typically attaches to the camera head of elongated portion 46, mentioned above. Detachable distal tip 42 contains viewing optics 44 which are used in combination with probe optics 15 to guide and focus light received from the viewed surface or object (not shown) onto imager 12.

The elements shown in tip 42 could alternatively be located on elongated portion 46. These elements include viewing optics 44, at least one emitter module 37, at least one intensity-modulating element 38, and light passing element 43. In addition, the at least one light emitter module 37, comprising a plurality of light emitters, could be fixedly attached to insertion tube 40 while the at least one intensity-modulating element is disposed on detachable tip 42. In this case, precise and repeatable alignment between detachable tip 42 and elongated portion 46 is required, but it is advantageous because allows different fields of view while eliminating the need for contacts between elongated portion 46 and detachable tip 42.

Shown in FIG. 1, imager 12 is located at the distal end of insertion tube 40. Alternatively, imager 12 may be located at the proximal end of insertion tube 40. The alternative configuration may be suitable, for example, in a rigid borescope or fiberscope.

Imager 12 obtains at least one image of the viewed surface. Imager 12 may comprise, for example, a two-dimensional array of light-sensitive pixels that outputs a video signal in response to the light level sensed at each pixel. Imager 12 may comprise a charge-coupled device (CCD), complementary metal-oxide-semiconductor (CMOS) image sensor, or other devices of similar function. The video signal is buffered by electronics 13 and transferred to imager interface electronics 31 via signal line 14. Imager interface electronics 31 may include, for example, power supplies, a timing generator for generating imager clock signals, an analog front end for digitizing the imager video output signal, and a digital signal processor (DSP) 51 for processing the digitized imager video data into a more useful format for video processor 50.

Video processor 50 performs various functions not limited to image capture, image enhancement, graphical overly merging, and video format conversion and stores information relating to those functions in video memory 52. Video processor 50 may comprise field-programmable gate array (FPGA), camera DSP, or other processing elements and provides information to and receives information from central processing unit (CPU) 56. The provided and received information may relate to commands, status information, video, still images, and/or graphical overlays. Video processor 50 also outputs signals to various monitors such as computer monitor 22, video monitor 20, and integral display 21. Video processor 50 also comprises motion detection module 53 and/or fringe contrast determining function 54. Alternatively, CPU 56 or microcontroller 30, described below, or probe electronics 48 comprising camera control electronics (not shown), may include motion detection module 53.

When connected, each of computer monitor 22, video monitor 20, and/or integral display 21 typically display images of the object or surface under inspection, menus, cursors, and measurement results. Computer monitor 22 is typically an external computer type monitor. Similarly, video monitor 20 typically includes an external video monitor. Integral display 21 is integrated and built into probe system 10 and typically comprises a liquid crystal display (LCD).

CPU 56 preferably uses both program memory 58 and non-volatile memory 60, which may include removable storage devices. CPU 56 may also use volatile memory such as RAM for program execution and temporary storage. A keypad 64 and joystick 62 convey user input to CPU 56 for such functions as menu selection, cursor movement, slider adjustment, and articulation control. Computer I/O interface 66 provides various computer interfaces to CPU 56 such as USB, Firewire, Ethernet, audio I/O, and wireless transceivers. Additional user devices such as a keyboard or mouse may be connected to computer I/O interface 66 to provide user control. CPU 56 generates graphical overlay data for display, provides recall functions and system control, performs phase-shift analysis and measurement processing, and provides image, video, and audio storage. CPU 56 and the previously discussed video processor 50 may be combined into one element of probe system 10. In addition, components of probe system 10 including, but not limited to, CPU 56 and video processor 50 may be integrated and built into probe system 10 or, alternatively, be externally located.

Referring to the at least one emitter module 37, light from the at least one emitter module 37 projects at least one structured-light pattern on the surface suitable for phase-shift analysis. The structured-light pattern preferably comprises parallel light and dark lines comprising sinusoidal intensity profiles. Line patterns having square, trapezoidal, triangular, or other profiles may be projected on the surface as well when used with appropriate phase-shift analysis to determine phase of the pattern. The pattern may also comprise other than straight, parallel lines. For example, curved lines, wavy lines, zigzagging lines, or other such patterns may be used with appropriate analysis.

The structured-light pattern projected from the at least one emitter module 37 may be created a number of ways. Emitter module 37 may comprise at least one light emitting element formed to include appropriate parallel light and dark lines. Light from the light emitting element may be passed through intensity modulating element 38. Alternatively, emitter module 37 may comprise a plurality of light emitters. The plurality of light emitters may be strategically positioned to form a structured-light pattern on the surface and/or light from the plurality of light emitters may be passed through intensity modulating element 38. In an embodiment of the present invention, intensity modulating element 38 comprises a line grating, which creates a structured-light pattern when light from emitter module 37 passes through to the surface or object (not shown).

A plurality of fringe sets are projected from the probe onto the viewed surface or object. A fringe set comprises at least one structured-light pattern. The structured-light pattern of one fringe set exhibits a spatial or phase-shift relative to the structured-light patterns of other fringe sets. The structured-light pattern preferably comprises parallel light and dark lines comprising sinusoidal intensity profiles. Line patterns having square, trapezoidal, triangular, or other profiles may be projected on the surface as well when used with appropriate phase-shift analysis to determine phase of the pattern. The pattern may also comprise other than straight, parallel lines. For example, curved lines, wavy lines, zigzagging lines, or other such patterns may be used with appropriate analysis.

When emitter module 37 comprises a plurality of light emitters, a fringe set comprises a structured-light pattern projected when one emitter group comprising a group of at least one light emitter is emitting light. In other words, a different subset of the plurality of light emitters emits light to project each of a plurality of structured-light patterns. The plurality of light emitters of emitter module 37 are positioned such that the structured-light pattern projected when one emitter group is emitting light exhibits a spatial or phase-shift relative to the structured-light patterns projected when other emitter groups are emitting light.

Light from the plurality of light emitters disposed on detachable tip 42 is passed through at least one intensity modulating element 38 to alter the distribution of light and project at least one structured-light pattern on the viewed surface suitable for phase-shift analysis. In one embodiment, the plurality of light emitters comprising an emitter group are spaced apart along the axis perpendicular to the lines on the line grating by a distance equal to an integer number of periods of the line grating. As a result, when the plurality of light emitters comprising one emitter group are simultaneously emitting light, the structured-light patterns produced by each of the multiple emitters sum together. This forms a brighter line pattern than would be generated by a single emitter element.

In another embodiment, the plurality of light emitters in an emitter group are arranged in a line parallel to the lines on the line grating and are electrically connected in series. This approach reduces the current needed to achieve a given light output relative to the current that would be required with a single emitter. This is beneficial as the emitter power is generally supplied through small wires having significant resistance, and reducing the drive current reduces the power dissipated in the wires and supplied by the emitter drive circuit.

A plurality of light emitting diodes (LEDs) may comprise the plurality of light emitters of the at least one emitter module 37. LEDs are practical in probe system 10 at least because LEDs offer consistent, uniform illumination, no speckling, and fast switching between fringe sets. However, any light emitting source(s) offering the qualities mentioned above are sufficient for use in probe system 10. Other such light sources include, but are not limited to, organic LEDs, plasma elements, fiber coupled lasers, and laser arrays.

The at least one emitter module 37 on detachable tip 42 may further comprise electronics for control/sequencing of emitters, sensing temperature, and storage/retrieval of calibration data. The at least one emitter module 37 may include a heat sink made of a ceramic or metal, for example, to reduce the temperature rise of the plurality of light emitters.

System 10 further comprises contacts 36 that electrically couple elongated portion 46 to detachable tip 42 through the camera head. Contacts 36 may be spring loaded and also provide electrical power from drive conductor 35 to emitter module 37. In an embodiment of the invention, drive conductor 35 carries power from emitter drive 32 to the plurality of light emitters disposed on the distal end of insertion tube 40. Drive conductor 35 comprises one or more wires and may be incorporated with signal line 14 in a common outer jacket (not shown). Drive conductor 35 may also share conductors with signal line 14 and/or utilize the insertion tube 40 structure for carrying current. Emitter drive 32 includes, for example, an adjustable current source with a variable on time to compensate for light emitters with differing power capabilities and efficiencies.

Discussed above, video processor 50 or CPU 56 comprises a brightness or fringe contrast determining function 54 to determine whether one emitter or multiple emitters should be enabled for each emitter group. In an embodiment of the present invention, brightness determining function 54 communicates with emitter drive 32 to selectively transmit current through specific wires connected to emitter module 37 to light an appropriate number of emitters per emitter group. Further control over brightness can be achieved by varying the drive level applied to the emitters or the duration of time the emitters are driven.

When brightness determining function 54 is located separately from emitter drive 32 one drive wire of drive conductor 35 connects emitter drive 32 to emitter module 37, and one or more control wires (not shown) controlled by brightness determining function 54 are also connected to emitter module 37. A circuit (not shown) included on emitter module 37 can selectively connect one or multiple emitters to the drive wire in response to signals on the control wire. Alternatively, when emitter drive 32 comprises brightness determining function 54, drive conductor 35 comprises one or more drive wires (not shown) per emitter. In this case, brightness determining function 54 selectively transmits current through specific drive wires of drive conductor 35 to light an appropriate number of emitters per emitter group.

In an embodiment of the invention, at least one calibrating-light pattern is projected onto the viewed surface or object. Projecting light from at least one of the plurality of light emitters may be used to create the at least one calibrating-light pattern on the surface or object. The calibrating-light pattern may comprise at least one structured-light pattern, and passing light from at least one of the plurality of light emitter through intensity modulating element 38 may create at least one calibrating-light pattern on the object. The calibrating-light pattern may include, but is not limited to, angled lines, a single line, a plurality of lines, a dot, a plurality of dots, and a plurality of parallel light and dark lines. It can be appreciated that fringe sets' and calibrating-light patterns may be projected from the same emitter module 37. This may be accomplished, for example, by spacing apart fringe set emitters and calibrating pattern emitters and passing light from them through separate areas of intensity modulating element 38.

In another embodiment of the present invention, a first projection set and a second projection set is projected onto a surface. A projection set comprises at least one fringe set comprising a structured-light pattern. When a projection set comprises a plurality of fringe sets, the structured-light pattern of one fringe set of the first projection set exhibits a phase-shift relative to the structured-light patterns of the other fringe sets of the first projection set. Similarly, the structured-light pattern of one fringe set of the second projection set exhibits a phase-shift relative to the structured-light patterns of other fringe sets of the second projection set. Typically, the first projection set is projected from one side of viewing optics 44 and the second projection set is projected from the other side of viewing optics 44. Depending on the configuration of detachable tip 42, a first projection set may alternatively be projected from the top of viewing optics 44 and a second projection set may be projected from the bottom of viewing optics 44, or vise versa. Even if insertion tube 40 is rotated, the first and second projection sets are projected from opposite positions or angles relative to the FOV. Therefore, the first projection set may be projected from any position or angle around viewing optics 44 that is opposite that of the second projection set.

Figure 2:
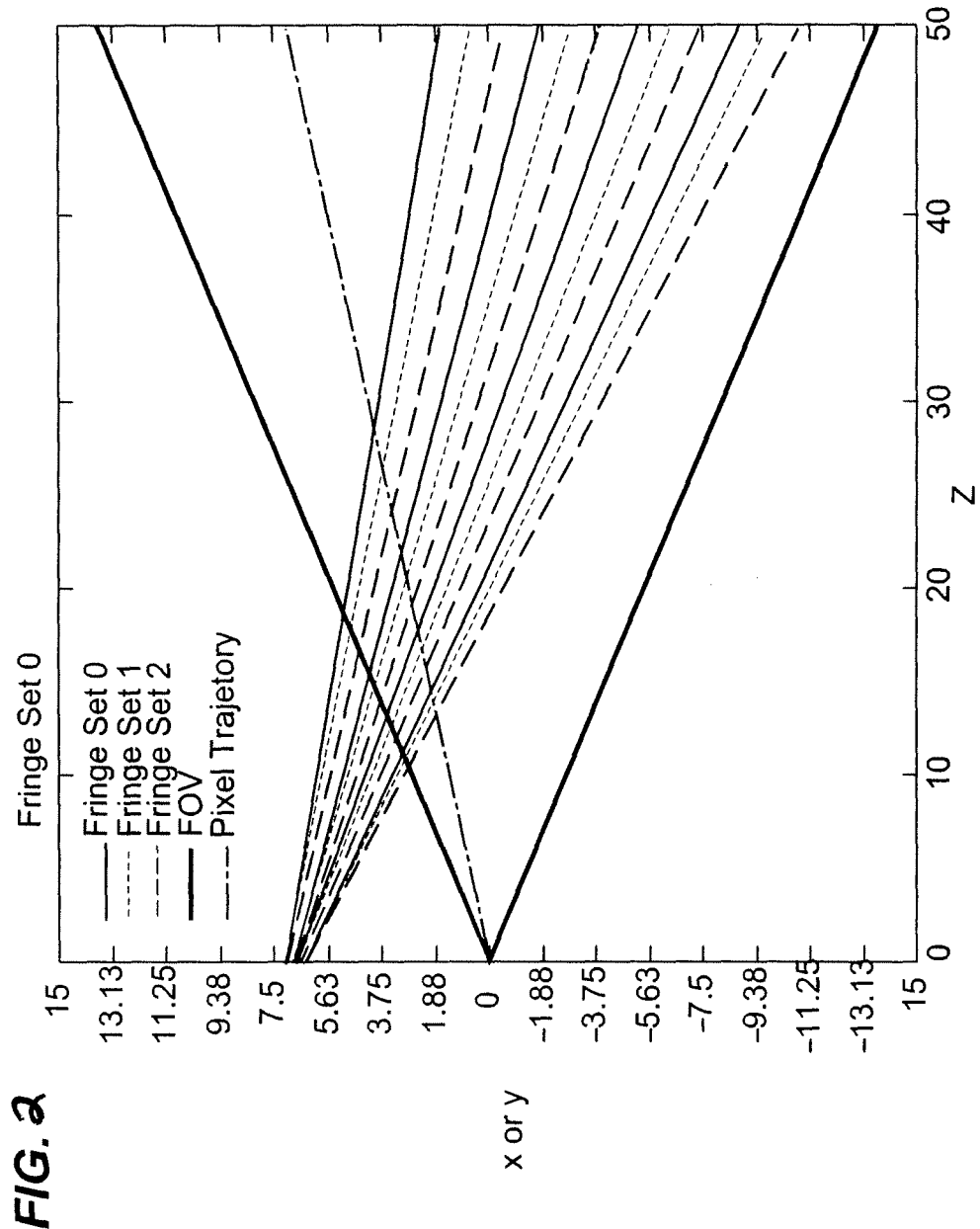
FIG. 2 is a graph showing the trajectory of an exemplary projection set projected from one side of the FOV.

Fringe sets 0; 1, and 2 of FIG. 2 comprise an exemplary projection set. In the case of FIG. 2, a plurality of fringe sets comprise the projection set. When a projection set comprises a plurality of fringe sets, the plurality of fringe sets comprising the projection set are typically projected from approximately the same origin relative to the FOV.

Figure 3:
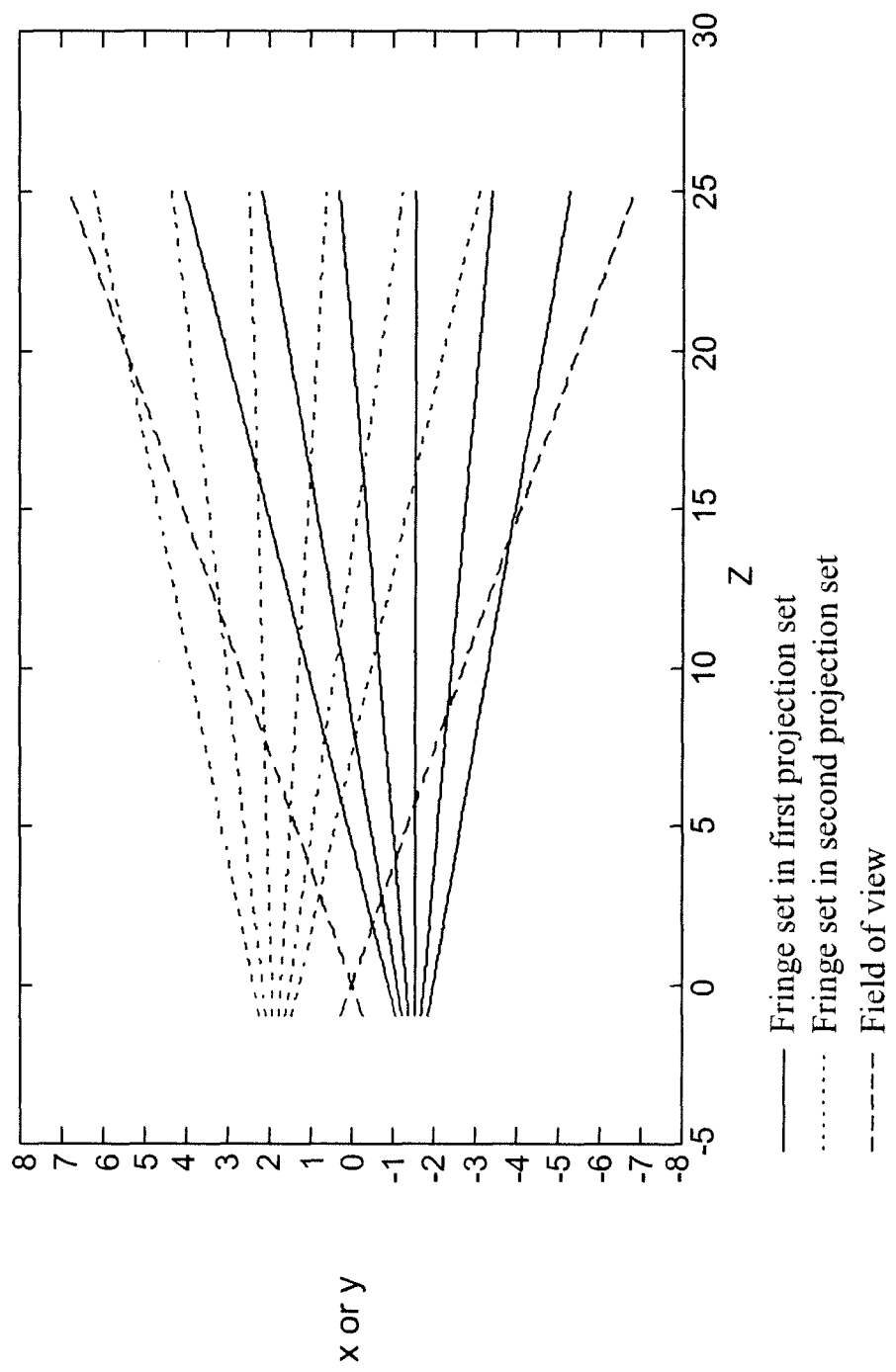
FIG. 3 is a graph showing the trajectory of the structured-lines of one fringe set in each of a first and second exemplary projection set relative to a field of view.

To further illustrate this, FIG. 3 shows a graph of two fringe sets. Each fringe set is a projection from opposite sides of the FOV. The fringe set in FIG. 3 represented by the solid lines projected from one side of the FOV comprises a first projection set, while the fringe set in FIG. 3 represented by the dashed lines projected from the other side of the FOV comprises a second projection set. Regarding the exemplary case of FIG. 3, only one fringe set per each projection set is shown; however a plurality of fringe sets may comprise each projection set. In an embodiment of the invention, a projection set comprises a plurality of fringe sets, each fringe set comprising a structured-light pattern, wherein the light pattern of one fringe set exhibits a phase-shift relative to the light patterns of the other fringe sets. When a first projection set and a second projection set are projected, a first image set and a second image set are captured. The first image set comprises fringe set images of the first projection set, and the second image set comprises fringe set images of the second image set, where one fringe set is projected onto the surface or object per image.

The probe operates in measurement mode when the at least one structured-light pattern is projected onto the surface. In an embodiment of the invention, emitter module 37 is enabled to project at least one structured-light pattern on the surface during measurement mode. During measurement mode, CPU 56 or video processor 50 captures a plurality of measurement mode images wherein the at least one structured-light pattern is projected onto the object. The measurement mode images may comprise fringe sets where no more than one fringe set is projected onto the object per measurement mode image. Measurement mode images of that sort are also referred to herein as fringe set images. Phase-shift analysis may then be performed directly on the plurality of fringe set images.

The probe operates in inspection mode when inspection light source 23 is enabled. Light is projected from inspection light source 23 onto a surface or object. During inspection mode, the at least one structured-light pattern may be absent. Generally, at least one image, referred to herein as an inspection mode image, is captured when light is projected from inspection light source 23 onto the viewed surface or object. Inspection light source 23 outputs relatively uniform light or diffuse illumination light from the distal end of insertion tube 40. The elements that produce and deliver light during inspection mode may collectively be referred to as an inspection light delivery system. In one embodiment, the inspection light delivery system comprises inspection light source 23, source fiber bundle 24, shutter mechanism 34, probe fiber bundle 25, and light passing element 43. In other embodiments, the inspection light delivery system may comprise very different elements such as, in the case of distally-located white LEDs, an LED drive circuit that can be disabled or provides an adjustable output current, wires for delivering power to the LEDs, the LEDs themselves, and a protective element to protect the LEDs. In another embodiment, the inspection light delivery system comprises a proximal LED coupled to a fiber bundle, which delivers light to the distal end of insertion tube 40, and an LED drive circuit.

Referring again to measurement mode, the intensity of light output from the inspection mode light delivery system originating from light source 23 is automatically decreased or disabled during measurement mode to avoid reducing the contrast of the at least one projected structured-light pattern. For example, CPU 56 may be configured to give an original command to turn off light source 23 electronically prior to projecting the at least one structured-light pattern through an enable/disable input to light source 23. Inspection light source 23 may then be automatically enabled, for example, electronically after a plurality of measurement mode images are captured or upon exiting measurement mode.

Similarly, CPU 56 may also be configured to give an original command to turn on or off light from the inspection delivery system through the use of shutter mechanism 34. Shutter mechanism 34 is configured to allow light output from the inspection light delivery system during inspection mode or regular inspection and block or otherwise inhibit light output originating from inspection light source 23 during measurement mode. Shutter mechanism 34 includes, for example, a solenoid or motor driven mechanical shutter or an electric light source disabler. When shutter mechanism 34 allows light from inspection light source 23 to pass, shutter mechanism 34 is in an open position. When shutter mechanism 34 blocks light from inspection light source 23, shutter mechanism 34 is in a closed position. During inspection mode, shutter mechanism 34 is configured to be in an open position. In contrast, during fringe set projection, shutter mechanism 34 is configured to be in a closed position. The location of shutter mechanism 34 can vary based on its implementation. In an embodiment of the invention, when shutter mechanism 34 allows light to pass, probe fiber bundle 25 delivers light to the surface or inspection site via light passing element 43.

Inspection light source 23 is typically a white light source, but may comprise any appropriate light source for a probe such as a mercury or metal halide arc lamp, halogen lamp, laser/phosphor system, or LED based light source which could be either proximally or distally located. When a fiber based light source is used, source fiber bundle 24 may be included in system 10. Source fiber bundle 24 comprises a non-coherent or semi-coherent fiber optic bundle and transmits light to shutter mechanism 34. Alternatively, source fiber bundle 24 may be omitted, and shutter mechanism 34 may be located directly between inspection light source 23 and probe fiber bundle 25. Probe fiber bundle 25 comprises a non-coherent fiber optic bundle. Light passing element 43 comprises a glass cane, formed fibers, and/or distribution control features such as lenses or a diffuser.

In some cases, projected light patterns in captured measurement mode images can be distracting and can make it more difficult for operators to see details on the viewed object. It is thus desirable to allow the operator to view a normal inspection mode image while placing measurement cursors rather than a measurement mode image that includes one or more structured-light patterns. Preferably, at least one counterpart inspection mode image and at least one counterpart measurement mode images are captured. The at least one counterpart measurement mode image comprises at least one of the plurality of measurement mode images, and the at least one counterpart inspection mode image comprises at least one inspection mode image captured in close time proximity to the at least one counterpart measurement mode image. Inspection mode images and measurement mode images captured in close proximity are referred to herein as counterpart images. Ideally, counterpart images comprise images of an object in the same position relative to the FOV.

Capturing counterpart images in close time proximity is advantageous at least because the relative movement between the probe's distal tip and the viewed object between the captures the counterpart images is minimized. Geometrical features, such as defects and edges, will appear in the same position in the counterpart images so that the locations of cursors positioned on an inspection-mode image correspond to the same points on the viewed object in the measurement-mode images. In an embodiment of the invention, motion detection module 53 analyzes inspection mode and measurement mode counterpart images.

Motion detection module 53 may be configured to analyze the images once all of the images have been captured. Alternatively, motion detection module 53 may be configured to analyze the images sequentially after the capture of each image. Motion detection module 53 is configured to automatically detect probe and/or surface movement between measurement mode images, also referred to herein as fringe set images or the images captured comprising structured-light patterns. Motion detection module 53 may be configured to compare only inspection mode images or only measurement mode images. Furthermore, motion detection module 53 may optionally be configured to compare at least one measurement mode image with its counterpart inspection mode image(s). In an embodiment of the invention, counterpart inspection mode image(s) may be captured at the beginning and/or the end of its counterpart measurement mode capture sequence.

Motion detection module 53 could be further configured to compare one or more captured images from each of two or more successive measurement mode capture sequences such that images having the same illumination and/or structured light patterns present may be compared rather than attempting to compensate for differences in pattern position or illumination. The term "measurement mode capture sequence" used herein is defined as the capture of a plurality of structured-light images, each captured image comprising one projected fringe set. During a measurement mode capture sequence a plurality of measurement mode images are captured.

Probe system 10 is configured to detect relative movement between the probe and the surface or object between the captures of two or more of a plurality of images. In an embodiment of the invention, motion detection module 53 is configured to analyze the images captured and compute a motion metric indicative of relative movement between the probe's distal tip and the surface or object between the captures of two or more of a plurality of images. These images may comprise the first and the last of a plurality of images. The first of the plurality of images is either an inspection mode image or a measurement mode image. Similarly, the last of the plurality of images is either an inspection mode image or a measurement mode image. If the motion metric indicates a high probability of movement, the capture of the plurality of images is repeated until either the motion metric indicates a low probability of movement or a pre-determined timeout occurs. For example, if the motion metric indicates a high probability of movement between counterpart measurement mode and inspection mode images, the capture of the measurement mode and inspection mode image(s) is repeated until the motion metric indicates a low probability of movement or a pre-determined timeout occurs. However, re-capture of the entire plurality of images may not always be necessary.

The value of the motion metric can depend upon the implementation of motion detection. The metric could be pixels of movement, in which case, the metric may be limited to a one pixel movement, for example, for indicating a low probability of movement. In that case any metric representing a movement greater than one pixel would indicate a high probability of movement. The metric limit for a low probability of movement could also be experimentally determined. Among others, one method for experimentally determining metric limits includes using a root mean square (RMS) difference between brightness values.

Figure 4:
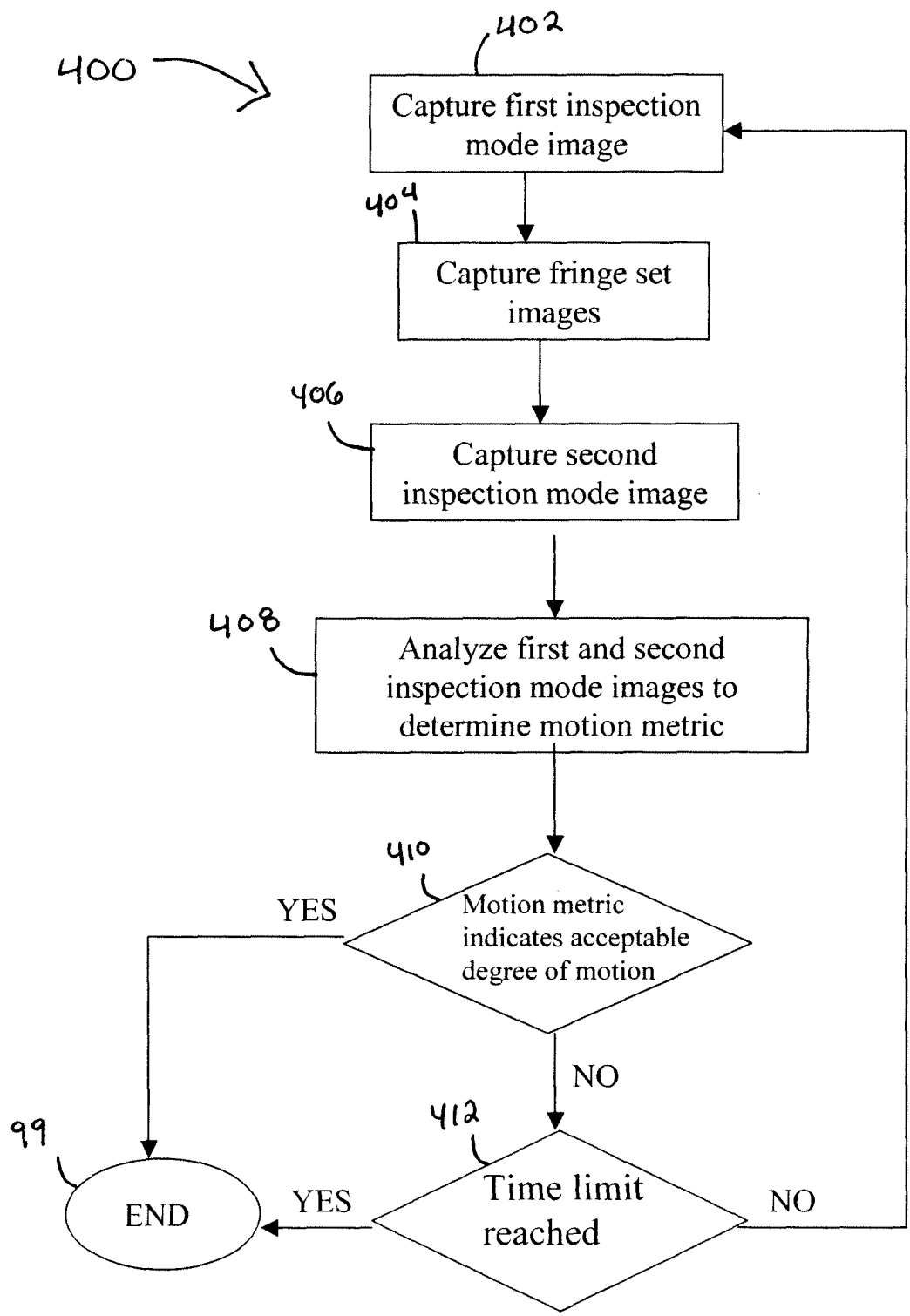
FIG. 4 is a flow chart illustrating an exemplary embodiment of the steps involved in motion detection.

FIG. 4 is a flow chart illustrating an exemplary embodiment of the steps involved in motion detection. Borescope/endoscope or probe system 10 shown in FIG. 1 is configured to perform the steps indicated in method 400. Method 400 may be implemented when probe system 10 is in inspection mode, and the CPU 56 receives a command requesting measurement. An operator may request measurement by pressing a button (not shown) on the probe system 10 or selecting a menu item from, for example, integral display 21.

Once the measurement command is received, at step 402, CPU 56 or video processor 50 captures a first inspection mode image. CPU 56 then sends a command to microcontroller 30 to enter measurement mode. Microcontroller 30 controls emitter drive 32 to perform a measurement mode capture sequence. At step 404, CPU 56 or video processor 50 captures measurement mode images. At least one measurement mode image is captured per structured-light pattern or fringe set. An operator may pre-program the specifics of the measurement mode capture sequence before the implementation of method 400 by selecting a menu item from integral display 21. For example, the operator may desire the capture of a plurality of measurement mode images per structured-light pattern or fringe set. In addition, those images of the same structured-light pattern or fringe set may be captured at the same brightness level or at different brightness levels depending on the analysis and/or mapping desired.

After the measurement mode images are captured, emitter drive 32 is disabled by microcontroller 30, and microcontroller 30 configures DSP 51 for inspection mode. At step 406, CPU 56 or video processor 50 captures a second inspection mode image. Motion detection module 53 then analyzes the first and second inspection mode images to determine a motion metric at step 408. If the motion metric indicates an unacceptable degree of motion, and the pre-set time limit is not reached, steps 402-412 are repeated until the motion metric indicates an acceptable degree of motion or the pre-set time limit is reached. Alternatively, if the motion metric indicates an unacceptable degree of motion at step 410, and the pre-set time limit is reached at step 412, the process ends at step 99. If the motion metric indicates an acceptable degree of motion, the process ends at step 99.

In another embodiment of the invention, motion detection module 53 is configured to analyze the images captured based on techniques such as high-frequency detail position comparison. Points in the images that include fast transitions in brightness can be identified in the first image in the sequence, and those points can be checked in one or more subsequent images to determine whether the fast transitions still occur at the same points; This approach can accommodate differences in illumination as would exist between measurement mode and inspection mode images. Images captured under the same lighting conditions, such as inspection-mode images captured before and after the counterpart measurement-mode images, can be simply subtracted from one another to determine whether the image has substantially changed.

Figure 5:
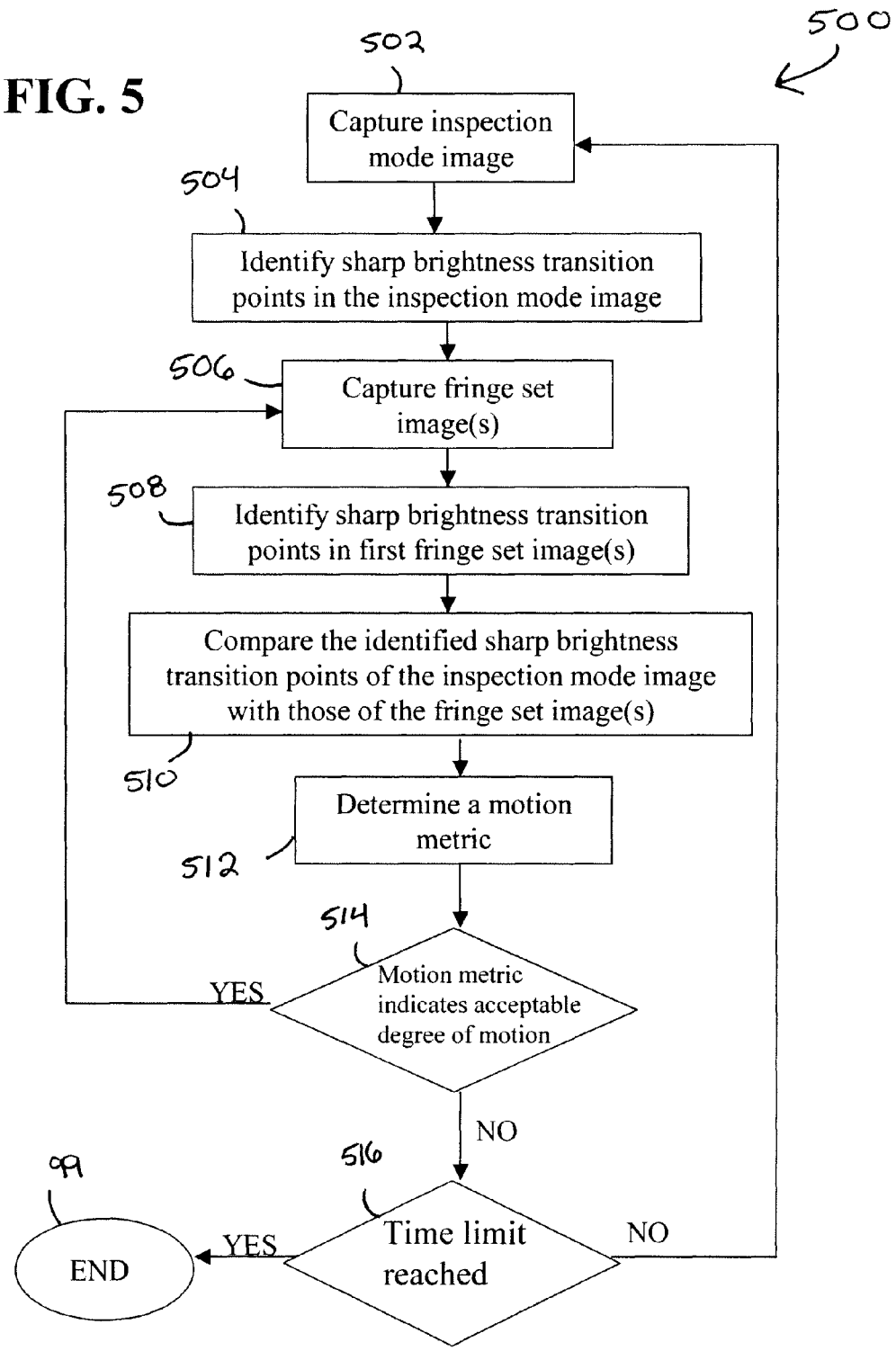
FIG. 5 is flow chart illustrating an exemplary alternative embodiment of the steps involved in motion detection.

FIG. 5 is a flow chart illustrating an exemplary alternative embodiment of the steps involved in motion detection. Borescope/endoscope or probe system 10 shown in FIG. 1 is configured to perform the steps indicated in method 500. Method 500 may be implemented when probe system 10 is in inspection mode, and the CPU 56 receives a command requesting measurement. An operator may request measurement by pressing a button (not shown) on the probe 10 or selecting a menu item from, for example, integral display 21.

Once the measurement command is received, at step 502, CPU 56 or video processor 50 captures an inspection mode image. At step 504, the CPU 56 or video processor 50 identifies sharp brightness transition points in the inspection mode image captured at step 502. CPU 56 then sends a command to microcontroller 30 to enter measurement mode. In an embodiment of the invention, microcontroller 30 controls emitter drive 32 to illuminate one emitter group to project a first fringe set. At step 506, CPU 56 or video processor 50 captures the first fringe set images. At least one measurement mode image is captured for the first fringe set. At step 508, the CPU 56 or video processor 50 identifies sharp brightness transition points in at least one of the first fringe set images captured at step 506.

Motion detection module 53 then compares the identified sharp brightness transition points of the inspection mode image with those of the fringe set image(s) at step 510. At step 512 motion detection module 53 determines a motion metric based on that comparison. If the motion metric indicates an unacceptable degree of motion at step 514, and the time limit is reached at step 516, the process ends at step 99.

If the motion metric indicates an unacceptable degree of motion, and the pre-set time limit is not reached, steps 502-516 are repeated until the motion metric indicates an acceptable degree of motion or the pre-set time limit is reached. Preferably, the sequence is repeated from step 502 to update the inspection mode image because it is unlikely that the measurement mode images will again line up with the original inspection image. Alternatively, the sequence may be repeated from step 506 to compare the captured fringe set images or two or more measurement mode images comprising the same structured-light pattern to each other until they all match up and then capture another inspection mode image at the end.

However, if the motion metric indicates an acceptable degree of motion, steps 506-514 are repeated for the second fringe set, then the third fringe set, etc. The process ends after sequencing through steps 506-514 for the last fringe set fringe set once all of the fringe set images are captured for that last fringe set and the motion metric indicates an acceptable degree of motion for the fringe set image(s) in the last fringe set.

Referring back to FIG. 1, the previously discussed imager interface electronics 31, emitter drive 32, and shutter mechanism 34 are included in the probe electronics 48. Probe electronics 48 may be physically separated from a main control unit or CPU 56 to provide more local control over probe-related operations. Probe electronics 48 further comprise calibration memory 33. Calibration memory 33 stores information relating to the optical system of detachable tip 42 and/or elongated portion 46 such as magnification data, optical distortion data, and pattern projection geometry data.

Calibration memory 33 stores information relating to the intensity relationship between the light projected from light source 23 and the light projected from emitter module 37. The intensity relationship between of the light projected by light source 23 and emitter module 37 can be pre-determined before any image capture. Typically, the brightness or intensity from light source 23 is greater than the brightness or intensity from emitter module 37. Therefore, the imager 12 exposure time and/or the analog gain applied to video signal output by imager 12 during inspection mode image capture should be different from those during measurement mode image capture.

Microcontroller 30, which controls shutter 34, communicates with CPU 56 and controls emitter drive 32 circuitry, and also communicates with imager interface electronics 31 to determine and set gain and exposure settings, and stores and reads calibration data from the calibration memory 33.

Probe system 10 further comprises one or more of a gain function, an exposure function, a gamma correction function and an edge enhancement function applied to image data originating from imager 12. Probe system 10 is configured to automatically adjust the parameters of at least one of said functions when switched between inspection mode image capture and measurement mode.

In an embodiment of the invention, the relative intensities of the light output by the inspection light delivery system and the structured-light patterns is determined during a calibration step and stored in calibration memory 33. DSP 51 included in imager interface electronics 31 may be configured to automatically adjust imager 12 exposure and front end analog gain to achieve optimal image brightness for inspection mode image capture.

Microcontroller 30 is configured to compute parameters of the exposure function and gain function settings from DSP 51 to use during measurement mode using exposure function and gain function values that are active during inspection mode. Microcontroller 30 is further configured to compute parameters of the exposure and gain functions according to a pre-determined intensity relationship between the light of the structured-light patterns and the light from inspection light source 23 and set DSP 51 to apply the adjusted exposure and gain settings to optimize image brightness for measurement mode image capture. For example, the parameters of the exposure and gain functions are adjusted such that the brightness in the plurality of fringe set images is similar to the brightness in the inspection mode image(s). This approach eliminates the time that would be required for DSP 51 to reach an appropriate image brightness after the switch if DSP 51 were left in automatic exposure and gain adjustment mode, which is desirable to minimize the likelihood of motion between image captures. After the measurement-mode images are captured, DSP 51 may be again configured for automatic gain and exposure adjustment to optimize image brightness for inspection-mode image capture.

Figure 6:
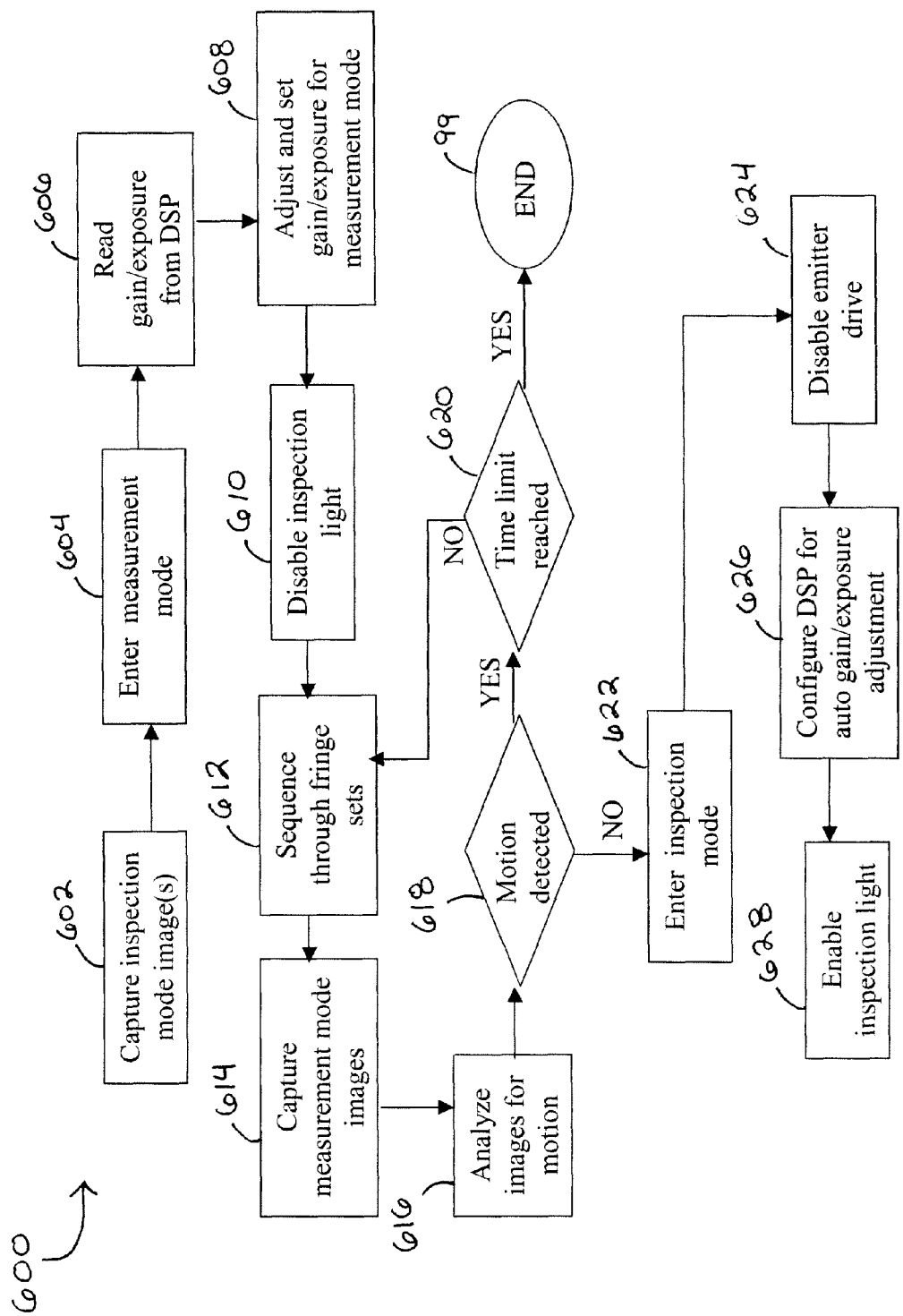
FIG. 6 is a flow chart illustrating an exemplary embodiment of the steps involved during an image capture sequence of the present invention.

FIG. 6 is a flow chart illustrating an exemplary embodiment of the steps involved during an image capture sequence of the present invention. The term "image capture sequence" used herein is defined as the capture of counterpart inspection mode and measurement mode images. The term "image capture sequence" is not to be confused with the term "measurement mode capture sequence" defined above.

Borescope/endoscope or probe system 10 shown in FIG. 1 is configured to perform the steps indicated in method 600. Method 600 may be implemented when probe system 10 is in inspection mode, and the CPU 56 receives a command requesting measurement. An operator may request measurement by pressing a button (not shown) on the probe 10 or selecting a menu item from, for example, integral display 21.

Once the measurement command is received, at step 602, CPU 56 or video processor 50 captures the inspection mode image(s). At step 604, CPU 56 sends a command to microcontroller 30 to enter measurement mode. At step 606, microcontroller 30 reads the analog gain and exposure from DSP 51, and at step 608, the microcontroller 30 adjusts the gain and exposure for measurement mode. Discussed above, the measurement mode DSP 51 settings may be adjusted according to a pre-determined intensity relationship between the inspection light delivery system and the structured light patterns. Further at step 608, microcontroller 30 sets DSP 51 to fixed gain and exposure based on the adjusted values. At step 610, the inspection light is disabled by microcontroller 30 or CPU 56 as discussed previously.

At step 612, microcontroller 30 controls emitter drive 32 to perform a measurement mode capture sequence. In an embodiment of the invention, performing a measurement mode capture sequence comprises sequencing through emitter groups, different subsets of light emitters, on frame boundaries while possibly adjusting on time or drive level to compensate for different emitter brightness levels. Furthermore, a drive level supplied to one subset light emitters may be adjusted to compensate for a temperature difference between that subset of light emitters and another subset of light emitters. Different emitter brightness levels may be due to differing emitter efficiencies or to heating of the emitters as the sequence progresses. For example, if the emitters are LEDs, the efficiency generally decreases as temperature increases. When the first LED is turned on, emitter module 37 is cooler than when the last LED is turned on. Thus, the last LED requires more drive current to achieve the same output as the first LED. The difference in drive levels may be predetermined through a calibration step. LED forward voltage drop also typically increases as temperature increases. Thus, microcontroller 30 in conjunction with emitter drive 32 may measure the LED forward drop to determine LED temperature to more accurately compensate for the efficiency change.

At step 614, CPU 56 or video processor 50 captures measurement mode images. At least one measurement mode image is captured per fringe set. In addition, a plurality of measurement mode images may be captured per fringe set such that measurement mode images of each fringe set are captured at the same brightness level; also, a plurality of measurement mode images may be captured per fringe set such that the plurality of fringe set images of at least one fringe set are captured at different brightness levels.

Motion detection module 53 analyzes the images for motion at step 616. If motion is detected at step 618, and the pre-set time limit is reached at step 620, the process ends at step 99. If motion is detected, and the pre-set time limit is not reached, steps 612-620 are repeated until motion is not detected or the pre-set time limit is reached. Alternatively, if motion is not detected at step 618, CPU 56 sends a command to microcontroller 30 to enter inspection mode. At step 624, emitter drive 32 is disabled by microcontroller 30. At step 626, microcontroller 30 configures DSP 51 for inspection mode by setting DSP 51 for automatic gain and exposure adjustment. At step 628, CPU 56 or microcontroller 30 enables inspection light output. After step 628, CPU 56 or video processor 50 may again capture inspection mode image(s), as in step 402. This marks the end of the image capture sequence. Method 600 may be repeated automatically to sequence through the steps a pre-determined number of times. Alternatively, an operator may manually command the repetition of method 600 by requesting measurement each time a new image capture sequence is desired.

Referring back to step 618 of FIG. 6, probe system 10 does not have to directly enter inspection mode if there is no motion detected at step 618. In another embodiment of the invention, if there is no motion detected at step 618, the user is given an option to either enter inspection mode at step 622 or to enter a measurement screen (not shown). The measurement screen displays a counterpart inspection mode image, preferably captured from step 602, while analysis or measurement is performed on the at least one counterpart measurement mode image, preferably captured from step 614. The measurement screen enables the placement of measurement cursors on the counterpart inspection mode image while the actual analysis or measurement is performed on data representing the at least one counterpart measurement mode image. Optionally, when entering the measurement screen, the emitter drive is disabled so that structured-patterns are not projected. The user can choose to enter inspection mode at any point desired while viewing the measurement screen to pick up at step 622. If the emitter drive was previously disabled from entering the measurement screen, step 624 is skipped. The sequence resumes at step 626, where microcontroller 30 configures DSP 51 for inspection mode by setting DSP 51 for automatic gain and exposure adjustment.

Probe system 10 is configured to change the parameters of imager 12 analog gain and exposure functions through DSP 51 when switched between inspection mode and measurement mode. Probe system 10 is also configured to automatically adjust other processing parameters of DSP 51, including, but not limited to, gamma correction and edge enhancement, when switched between inspection mode and measurement mode.

Regarding gamma correction, typically, imager 12 responds to light in a linear manner. A non-linear re-mapping of the intensity or luminance values is often performed by the DSP 51 to improve the perceived brightness uniformity for image display. Non-linear remapping of the intensity values of images captured during inspection mode may be desirable. However, it is preferable to perform phase-shift analysis on images representative of a linear response to light. Therefore, the linear response to light must be carried over from imager 12 to video processor 50 during measurement mode because phase-shift analysis is generally performed on the structured-light images captured during measurement mode. The probe system 10 is configured to decrease an effective level of gamma correction applied to pixels of at least one measurement mode image relative to the level of gamma correction applied during inspection mode. For example, a linear gamma DSP setting is enabled or switched on during measurement mode. During inspection mode, however, the linear gamma DSP setting is typically disabled, or set to be non-linear, to improve the perceived inspection-mode image quality.

Regarding edge enhancement, enabling edge enhancement artificially modifies the brightness linearity of an image. This is generally not desirable for images on which phase-shift analysis is performed as images representative of a linear response to light are preferred. Therefore, the edge enhancement function is disabled or switched off for measurement mode image capture, and may be enabled or switched on for inspection mode viewing and inspection mode image capture. Probe system 10 is configured to reduce an effective level of edge enhancement applied to pixels of at least one measurement mode image relative to the level of edge enhancement applied during inspection mode.

Further relating to image capture, it is preferable to perform phase-shift analysis on images with little to no random noise to improve measurement accuracy. To reduce random noise, probe system 10 may be configured to capture a plurality of measurement mode images with the same structured-light pattern or same fringe set present and average or sum two or more of those measurement mode images. The result is a plurality of composite images where only one fringe set is present in each composite image. These plurality of measurement mode images with the same structured-light pattern or same fringe set present may be captured with the same or similar brightness levels. When the composite image of a projected fringe set a result of summing rather than averaging, the dynamic range is increased and noise is reduced. Whether the composite images are a result of summing or averaging, phase-shift analysis and other processes can be performed on the composite images.

Furthermore, measurement mode images comprising the same structured-light pattern or same projected fringe set may be captured with different brightness or intensity levels. This is accomplished by either manually or automatically changing the emitter output intensity or duration, imager 12 exposure, analog gain, or some combination thereof.

Discussed above, fringe contrast determining function 54 is configured to determine whether one emitter or multiple emitters should be enabled for each emitter group. In order to change the light source intensity, for example, fringe contrast determining function 54 may further be configured to sequence between enabling one emitter and multiple emitters per emitter group to project light. Also discussed above, microcontroller 30 communicates with imager interface electronics 31 to determine and set gain and exposure settings. Similarly, microcontroller 30 may configure emitter drive 32 to alter the amount of power delivered to emitter module 37 and thus vary the intensities of the projected fringe sets.

A plurality of measurement mode images captured with different brightness or intensity levels comprising the same projected fringe set may be combined to effectively increase the dynamic range of the system. For example, an image may be captured of a shiny metal surface comprising a structured-light pattern. Reflective properties of the shiny metal surface may prevent adequate intensity levels in dark areas. Therefore, multiple images for each fringe set may be captured with different intensity levels so that, in at least some images, the dark areas are properly illuminated. Then, the captured images for each fringe set may be combined resulting in a single image for each fringe set with sufficient intensity levels across a larger portion of the image than could be achieved with a single image per fringe set.

CPU 56 or video processor 50 may be configured to analyze an inspection-mode image prior to capturing the measurement-mode images to determine brightness uniformity. The analysis may be performed by generating and evaluating a histogram of pixel luminance values. A histogram having most of the pixels in a middle brightness range would indicate that a single set of measurement-mode images would likely be adequate. A histogram having mostly very bright pixels and very dark pixels may indicate a highly reflective surface that would benefit from the merging of multiple measurement-mode image sequences captured at different brightness levels.

In an embodiment of the invention, multiple measurement mode images that comprise the same projected structured-light pattern or fringe set and are captured with different intensity levels are combined by evaluating each pixel intensity in the multiple images and selecting the set of pixels that best meets a set of criteria, such as maximum modulation, brightness values, or pixel unsaturation. Pixel values from more than one measurement mode image comprising the same structured-light pattern or same fringe set may be utilized to determine at least one geometric dimension of the surface or object.

The discussion above generally relates to image capture by probe system 10. The discussion below generally relates to the use and storage of those captured images.

In an embodiment of the invention, image(s) comprising structured-light patterns captured during measurement mode are hidden from the operator, and are used only for the actual analysis and measurement. For example, CPU 56 or video processor 50 creates an image file comprising data representing a counterpart inspection mode image and creates a hidden record within the image file comprising data representing its at least one counterpart measurement mode image. The counterpart inspection mode image can be displayed while the operator positions overlay cursors for determining geometric measurements of a viewed object while analysis is performed on the counterpart measurement mode image to determine the geometric measurement results. Therefore, the operator may command analysis or measurement while viewing an inspection mode image even though the analysis or measurement is performed on its counterpart measurement mode image or images. This can also be done prior to image storage, for example, as previously discussed in relation to FIG. 6, where the inspection mode image is displayed and the measurement images are processed.

The operator skill requirement is reduced by allowing the user to place cursors on a normal, inspection mode, image without having to worry about stereo matching, perpendicularity, shadow position, etc. The operator may use joystick 62 to place cursors on an inspection mode image displayed on integral display 21. Interchangeably with joystick 62, keypad 64 and/or computer I/O interface 66 may also be used to place cursors, and interchangeably with integral display 21, computer monitor 22 and/or video monitor 20 may also be used to display the inspection mode image.

Typically, when a measurement is performed on an image, and the image is saved, graphical overlay data is added to the image such as cursor positions, measurement results, accuracy indicators, etc. This graphical overlay must be removable to enable easy re-measurement at a later time where the non-graphical data related to the image is required. A method for storing image-specific data from a probe, specifically calibration data, is known from U.S. Pat. No. 7,262,797. It is further desirable to store measurement data, for example, relating to phase-shift analysis. Measurement data includes, but is not limited to the luminance portion of a structured-light image (luminance data), measurement cursor positions, merged image data, measurement types, results, accuracy indications, etc., calibration data, phase data, and phase-shift analysis data. Phase data may include data representing the phases of the structured-line patterns, for example wrapped phase, unwrapped phase, relative phase, and/or absolute phase. The co-pending application entitled Phase-Shift Analysis System and Method filed on Mar. 5, 2008 as U.S. Ser. No. 12/042800, which is incorporated herein by reference, discusses the implementation of phase data in phase-shift analysis. Phase-shift analysis data includes, but is not limited to, surface or object distance data (z values for each pixel, where z is the object distance from the probe), and point cloud data (x, y, z values for each pixel). As one skilled in the art should understand, the method disclosed in U.S. Pat. No. 7,262,797 should include the additional step of "writing measurement data to file."

Specifically, the system may include a geometric measurement mode in which a counterpart inspection mode image is displayed, an operator positions measurement cursors on the inspection mode image to identify measurement points, and CPU 56 computes and displays measurement results based on 3D data derived through phase-shift analysis performed on the counterpart measurement images utilizing calibration data. When the operator requests an image save, CPU 56 creates an image file. It merges overlay data with the inspection image data and saves the result in the image file such that when the file is opened by a standard image viewer, the inspection mode image and overlay are displayed. CPU 56 also creates hidden records in the image file. In these hidden records, it stores the inspection image data that was overwritten by the overlay data, referred to as overlay-replacement data, and measurement data. Thus, a custom software application can fully recover the original inspection mode image and has all the information needed to replicate the existing measurements and/or perform additional measurements or analysis.

Measurement data in bitmap and JPEG images captured using probe system 10 or an accompanying personal computer application is saved by CPU 56 or video processor 50. This allows images to have "destructive" overlays that are visible in the image using standard image viewing software, but which are removable by a custom application to present a clean image to the viewer or operator. The clean image can either be a measurement mode image or its counterpart inspection mode image. Storing luminance and measurement data in the image also allows the measurements to be repeated on the image using either the probe software or by a custom program, such as a PC-based software package.

Once images are captured and, optionally, stored by probe system 10, the image data can be used in many ways. For example, pixel values from the measurement mode images can be used to determine at least one geometric dimension of the object or surface. In addition, image data can be used for performing 3D geometric measurements or 3D visualization. The image data can also be exported or converted to a data format usable with 3D modeling software for detailed analysis or reverse engineering.

The construction and arrangement of systems and methods relating to image capture, as described herein and shown in the appended figures, is illustrative only and is not limited to a probe. Although only a few embodiments of the invention have been described in detail in this disclosure, those skilled in the art who review this disclosure will readily appreciate that many modifications are possible (e.g. variations in sizes, dimensions, structures, shapes and proportions of the various elements, values of parameters, mounting arrangements, use of materials, orientations, etc.) without materially departing from the novel teachings and advantages of the subject matter recited in the appended claims. Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the preferred and other exemplary embodiments without departing from the spirit of the embodiments of the invention as expressed in the appended claims. Therefore, the technical scope of the present invention encompasses not only those embodiments described above, but also those that fall within the scope of the appended claims.

What is claimed is:

1. A method for producing an image using a probe system having an imager and an inspection light source, and executed with a processor, the method comprising:
   operating the probe system in an inspection mode and a measurement mode;
   enabling the inspection light source during inspection mode and disabling the light source during measurement mode;
   enabling a light emitter drive during measurement mode;
   projecting a structured-light pattern using the light emitter drive during measurement mode;
   capturing, during inspection mode, at least one inspection mode image;
   capturing, during measurement mode, at least one measurement mode image wherein the structured-light pattern is projected onto an object;
   inserting a measurement point; and
   utilizing pixel values from the at least one measurement mode image and the measurement point to determine at least one geometric dimension of the object.

2. The method of claim 1, wherein the step of projecting a structured-light pattern using the light emitter drive during measurement mode further comprises the step of projecting a structured-light pattern comprising parallel light and dark lines having sinusoidal intensity profiles.

3. The method of claim 1 wherein the step of projecting a structured-light pattern using the light emitter drive during measurement mode further comprises the step of projecting a structured-light pattern comprising a fringe set, wherein no more than one fringe set is captured in each of the at least one measurement mode images.

4. The method of claim 3, wherein:
   the structured-light pattern of one fringe set exhibits a phase-shift relative to structured-light patterns of other fringe sets.

5. The method of claim 1, further comprising projecting at least one calibrating-light pattern onto the object.

6. The method of claim 1, further comprising:
   disabling the inspection light source during measurement mode by blocking light from the inspection light source using a shutter mechanism.

7. The method of claim 1, further comprising:
   automatically enabling the inspection light source upon exiting measurement mode.

8. The method of claim 1, further comprising:
   creating a single image file comprising a viewable image wherein at least one measurement cursor has been destructively overlaid; and
   creating at least one hidden record wherein the viewable image and at least one measurement point comprises a measurement cursor that is viewable using image viewer software, the at least one hidden record comprising at least one of overlay replacement data, measurement cursor positions, calibration data, structured light image data, phase data, point cloud data, and object distance data such that a custom program can perform geometric measurements on the viewable image.

9. The method of claim 1, wherein:
   capturing the at least one inspection mode image occurs when light from the inspection light source is projected onto the object.

10. The method of claim 1, further comprising:
    capturing a counterpart inspection mode image and at least one counterpart measurement mode image;
    wherein the at least one counterpart measurement mode image comprises at least one of the at least one measurement mode images; and
    wherein the counterpart inspection image comprises at least one inspection mode image captured in close time proximity to the at least one counterpart measurement mode image, the at least one inspection mode image comprising light from the inspection light source projected onto the object.

11. The method of claim 10, further comprising:
    entering a measurement screen wherein the counterpart inspection mode image is displayed which enables cursors to be placed for measurement to determine the at least one geometric dimension of the object.

12. The method of claim 1, further comprising applying one or more of a gain function, an exposure function, a gamma correction function, and an edge enhancement function to image data originating from the imager; and
    automatically adjusting the parameters of at least one of said functions when switched between inspection mode and measurement mode.

13. The method claim of 12, further comprising:
    computing parameters of the exposure function and the gain function to use during measurement mode using exposure function values and gain function values that are active during inspection mode.

14. The method of claim 12, further comprising:
    computing parameters of the exposure function and the gain function to use during measurement mode using a pre-determined intensity relationship between light of the structured-light pattern and light from the inspection light source.

15. The method of claim 12, further comprising:
    decreasing an effective level of gamma correction applied to pixels of the at least one measurement mode image relative to the level of gamma correction applied during inspection mode.

16. The method of claim 12, further comprising:
    reducing an effective level of edge enhancement applied to pixels of the at least one measurement mode image relative to the level of edge enhancement applied during inspection mode.

17. The method of claim 1, wherein the at least one measurement mode image comprises a plurality of measurement mode images comprising a same structured-light pattern; and
    wherein pixel values from more than one image of the plurality of measurement mode images comprising the same structured-light pattern are utilized to determine the at least one geometric dimension of the object.

18. The method of claim 17, further comprising capturing, with different levels of brightness, the plurality of measurement mode images comprising the same structured-light pattern.

19. The method of claim 17, further comprising capturing, with similar levels of brightness, the plurality of measurement mode images comprising the same structured-light pattern.

20. The method of claim 17, further comprising:
generating at least one composite image comprising two or more of the plurality of measurement mode images comprising the same structured-light pattern.

21. The method of claim 1, further comprising:
emitting light to project each of a plurality of structured-light patterns using a plurality of light emitters, wherein a different subset of the plurality of light emitters projects each of the structured-light patterns, and wherein the light emitter output intensity varying with emitter temperature, and supplying a drive level to one subset of the plurality of light emitters that are adjusting to compensate for a temperature difference between that subset of the plurality of light emitters and another subset of the plurality of light emitters.

22. A method for producing an image using a probe system having an imager coupled to an interface and a processor, the processor being coupled to a probe interface, a diffuse illumination source, a light emitter drive, the method comprising:
operating the probe system in an inspection mode and a measurement mode;
enabling the diffuse illumination light source during inspection mode;
enabling the light emitter drive during measurement mode;
projecting a structured-light pattern using the light emitter drive during measurement mode;
capturing, during inspection mode, at least one inspection mode image;
capturing, during measurement mode, at least one measurement mode image wherein the structured-light pattern is projected onto an object;
inserting a measurement point;
utilizing pixel values from the at least one measurement mode image and the measurement point to determine at least one geometric dimension of the object;
capturing two or more movement detection images; and
detecting relative movement between a probe and the object between captures of the two or more movement detection images.

23. The method of claim 22, wherein the step of projecting a structured-light pattern using the light emitter drive during measurement mode further comprises the step of projecting a structured-light pattern comprising parallel light and dark lines having sinusoidal intensity profiles.

24. The method of claim 22, wherein the step of projecting a structured-light pattern using the light emitter drive during measurement mode further comprises the step of projecting a structured-light pattern comprising a fringe set, wherein no more than one fringe set is captured in each of the at least one measurement mode images.

25. The method of claim 24, wherein:
the structured-light pattern of one fringe set exhibits a phase-shift relative to structured-light patterns of other fringe sets 26. The method of claim 22, further comprising projecting at least one calibrating-light pattern onto the object.

27. The method of claim 22, further comprising:
computing a motion metric indicative of the relative movement between the probe and the object between the captures of the two or more movement detection images.

28. The method of claim 27, further comprising:
repeating the capture of at least one of the movement detection images if the motion metric indicates a high probability of relative movement until either the motion metric indicates a low probability of relative movement or until a pre-determined timeout occurs.

29. The method of claim 22, further comprising:
capturing at least one movement detection image before the capture of the at least one measurement mode image; and
capturing at least one movement detection image after the capture of the at least one measurement mode image.

30. The method of claim 22, wherein the step of capturing, during measurement mode, at at least one measurement mode image further comprises the step of capturing a plurality of measurement mode images comprising a same structured-light pattern; and
wherein the two or more movement detection images comprises two or more of the plurality of measurement mode images comprising the same structured-light pattern.

31. The method of claim 22, further comprising:
inhibiting the diffuse illumination light during the capture of the at least one measurement mode image.

32. The method of claim 22, further comprising:
capturing a counterpart inspection mode image and at least one counterpart measurement mode image;
wherein the at least one counterpart measurement mode image comprises at least one of the at least one measurement mode images; and
wherein the counterpart inspection image comprises at least one inspection mode image captured in close time proximity to the at least one counterpart measurement mode image, the at least one inspection mode image comprising diffuse illumination light projected onto the object.

33. The method of claim 32, further comprising:
entering a measurement screen wherein the counterpart inspection mode image is displayed which enables cursors to be placed for measurement to determine the at least one geometric dimension of the object.

34. The method of claim 22, wherein the step of capturing, during measurement mode, at least one measurement mode image further comprises the step of capturing a plurality of measurement mode images comprising a same structured-light pattern; and
wherein pixel values from more than one image of the plurality of measurement mode images comprising the same structured-light pattern are utilized to determine the at least one geometric dimension of the object.

35. The method of claim 34, wherein the plurality of measurement mode images comprising the same structured-light pattern are captured with different brightness levels.

36. The method of claim 35, wherein the plurality of measurement mode images captured with different brightness levels are combined by choosing image pixels based on one of brightness values and modulation values.

37. The method of claim 34, wherein the plurality of measurement mode images comprising the same structured-light pattern are captured with similar brightness levels.

38. A probe system comprising:
an imager coupled to an interface and a processor, the processor being coupled to a probe interface, a diffuse illumination light source, a light emitter drive, wherein the probe system is configured to:
operate in an inspection mode and a measurement mode;
project diffuse illumination using the diffuse illumination source during inspection mode;
enable the light emitter drive during measurement mode;
project a structured-light pattern using the light emitter drive during measurement mode;
capture, during inspection mode, at least one inspection mode image;

capture, during measurement mode, at least one measurement mode image wherein the structured-light pattern is projected onto an object;
insert a measurement point; and
utilize pixel values from the at least one measurement mode image and the measurement point to determine at least one geometric dimension of the object.

* * * * *

UNITED STATES PATENT AND TRADEMARK OFFICE
CERTIFICATE OF CORRECTION

| | | |
|---|---|---|
| PATENT NO. | : 8,976,363 B2 | Page 1 of 1 |
| APPLICATION NO. | : 13/334239 | |
| DATED | : March 10, 2015 | |
| INVENTOR(S) | : Bendall et al. | |

It is certified that error appears in the above-identified patent and that said Letters Patent is hereby corrected as shown below:

In The Specification

In Column 3, Line 45, delete "user devices" and insert -- user I/O devices --, therefor.

In Column 5, Line 63, delete "sets'and" and insert -- sets and --, therefor.

In Column 10, Line 10, delete "points;" and insert -- points. --, therefor.

In The Claims

In Column 19, Line 55, in Claim 25, delete "sets" and insert -- sets. --, therefor.

Signed and Sealed this
Sixteenth Day of February, 2016

Michelle K. Lee
*Director of the United States Patent and Trademark Office*